(12) United States Patent
Dennis et al.

(10) Patent No.: US 8,932,852 B2
(45) Date of Patent: Jan. 13, 2015

(54) COMPOSITIONS AND METHODS OF TREATING INFLAMMATORY BOWEL DISEASE

(75) Inventors: James E. Dennis, Seattle, WA (US);
Thomas John Kean, Seattle, WA (US);
Inkap Ko, Clemmons, NC (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/390,491

(22) PCT Filed: Aug. 16, 2010

(86) PCT No.: PCT/US2010/045613
§ 371 (c)(1),
(2), (4) Date: Feb. 14, 2012

(87) PCT Pub. No.: WO2011/020095
PCT Pub. Date: Feb. 17, 2011

(65) Prior Publication Data
US 2012/0141564 A1   Jun. 7, 2012

Related U.S. Application Data

(60) Provisional application No. 61/233,910, filed on Aug. 14, 2009.

(51) Int. Cl.
| C12N 5/00 | (2006.01) |
| C12N 5/071 | (2010.01) |
| C07K 16/28 | (2006.01) |
| A61K 39/00 | (2006.01) |

(52) U.S. Cl.
CPC ......... *C07K 16/2803* (2013.01); *C07K 16/2836* (2013.01); *A61K 2039/505* (2013.01); *A61K 2039/507* (2013.01)
USPC ............................ 435/325; 435/372; 435/366

(58) Field of Classification Search
USPC .......................................... 435/325, 372, 366
See application file for complete search history.

(56) References Cited

FOREIGN PATENT DOCUMENTS

KR   10-2009-0065478   6/2009

OTHER PUBLICATIONS

Soriano et al., VCAM-1, but not ICAM-1 or MAdCAM-1 immunoblockade ameliorates DSS-induced colitis in mice. Laboratory Investigation, vol. 80. No. 10 (Oct. 2000) pp. 1541-1551.*
Karp et al., Mesenchymal stem cell homing: the devil is in the details. Cell Stem Cell, vol. 4. No. 3 (Mar. 6, 2009) pp. 206-216.*
Chamberlain et al., Concise review: mesenchymal stem cells: their phenotype, differentiation capacity, immunological features, and potential for homing. Stem Cells, vol. 25 (2007) pp. 2739-2749.*
Ko et al., Targeting mesenchymal stem cells to activated endothelial cells. Biomaterials, vol. 30 (online Apr. 17, 2009) pp. 3702-3710.*
Gonzalez-Rey et al., Human adult stem cells derived from adipose tissue protect against experimental colitis and sepsis. Gut, vol. 58 No. 7 (online Jan. 9, 2009) pp. 929-939.*
Ko et al., Targeting improves MSC treatment of inflammatory bowel disease. Molecular Therapy, vol. 18 No. 7 (Jul. 2010) pp. 1365-1372.*
Chamberlain, Giselle, et al., "Concise Review: Mesenchymal Stem Cells: Their Phenotype, Differentiation Capacity", Immunological Features, and Potential for Homing, Stem cells, v. 25 No. 11, pp. 2739-2749, (2007).
Pelletier, Ronald P., Importance of endothelial VCAM-1 for inflammatory leukocytic infiltration in vivo. The Journal of Immunology: official journal of the American Association of Immunologists, v. 149, No. 7, pp. 2473-2481 (1992).
Soriano, Antonio, et al., VCAM-1, but not ICAM-1 or MAdCAM-1, immunoblockade ameliorates DSS-induced colitis in mice. Laboratory investigation, v. 80 No. 10, pp. 1541-1552 (2000).
Spaeth, E., et al., "Inflammation and tumor microenvironments: defining the migratory itinerary of mesenchymal stem cells", Gene therapy , v. 15 No. 10 pp. 730-738 (2008).

* cited by examiner

*Primary Examiner* — Jon P Weber
*Assistant Examiner* — Kara Johnson
(74) *Attorney, Agent, or Firm* — Tarolli, Sundheim, Covell & Tummino LLP

(57) ABSTRACT

A method of treating a lymphocyte mediated inflammation in a subject including administering a therapeutically effective amount of a cell delivery composition to the subject, the cell delivery composition of the application including an immunosuppressive cell and a plurality of targeting moieties that bind to endothelial cell adhesion molecules expressed by endothelial cells as a result of a lymphocyte mediated inflammatory response in the subject, the targeting moieties coated on and linked to the immunosuppressive cell and enhancing adherence of the immunosuppressive cell to an endothelial cell at a site of lymphocyte mediated inflammation when administered to the subject systemically, wherein the cell delivery composition, suppresses lymphocyte mediated inflammation in the subject.

12 Claims, 7 Drawing Sheets

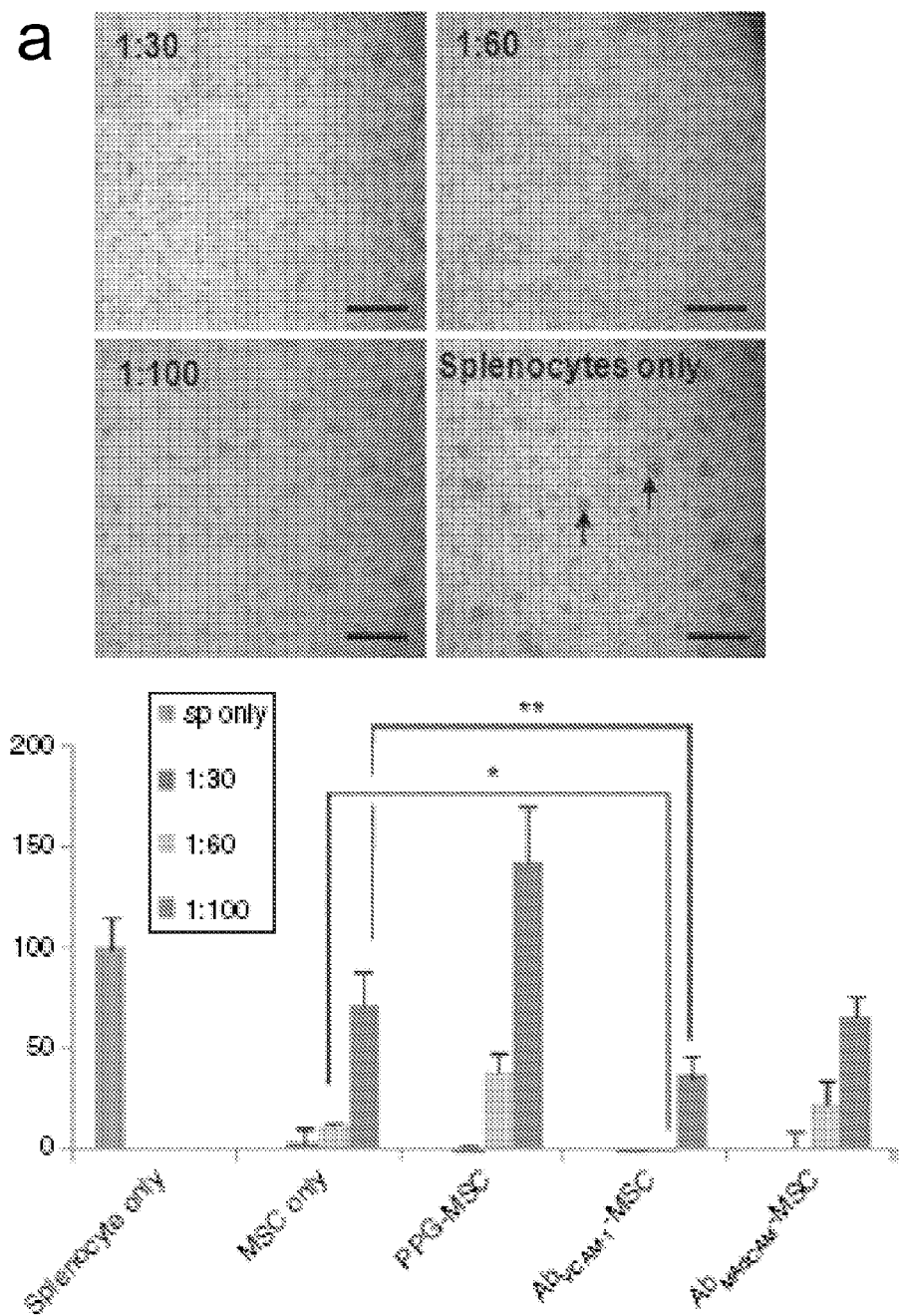
Figs. 1A-B

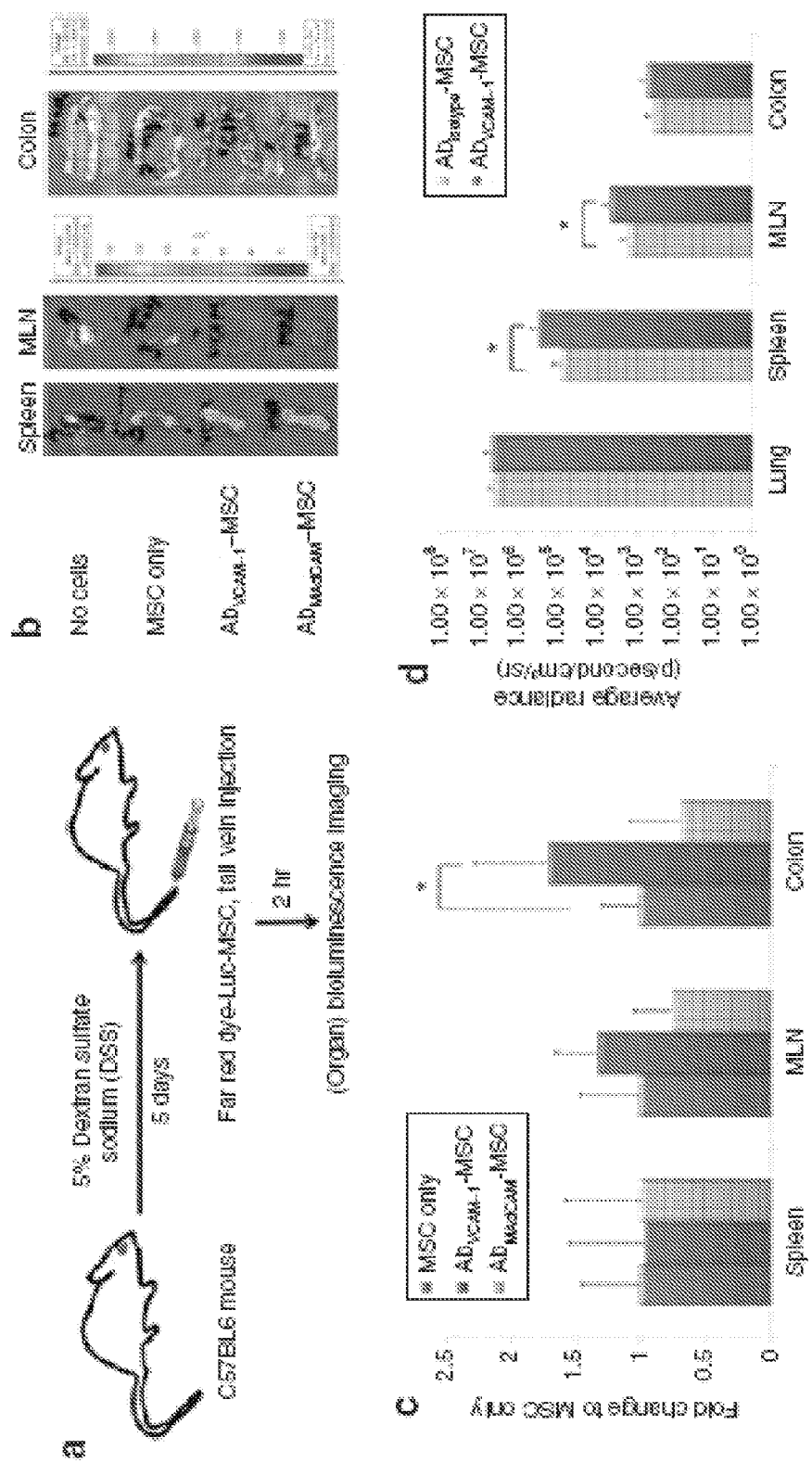
Figs. 2A-D

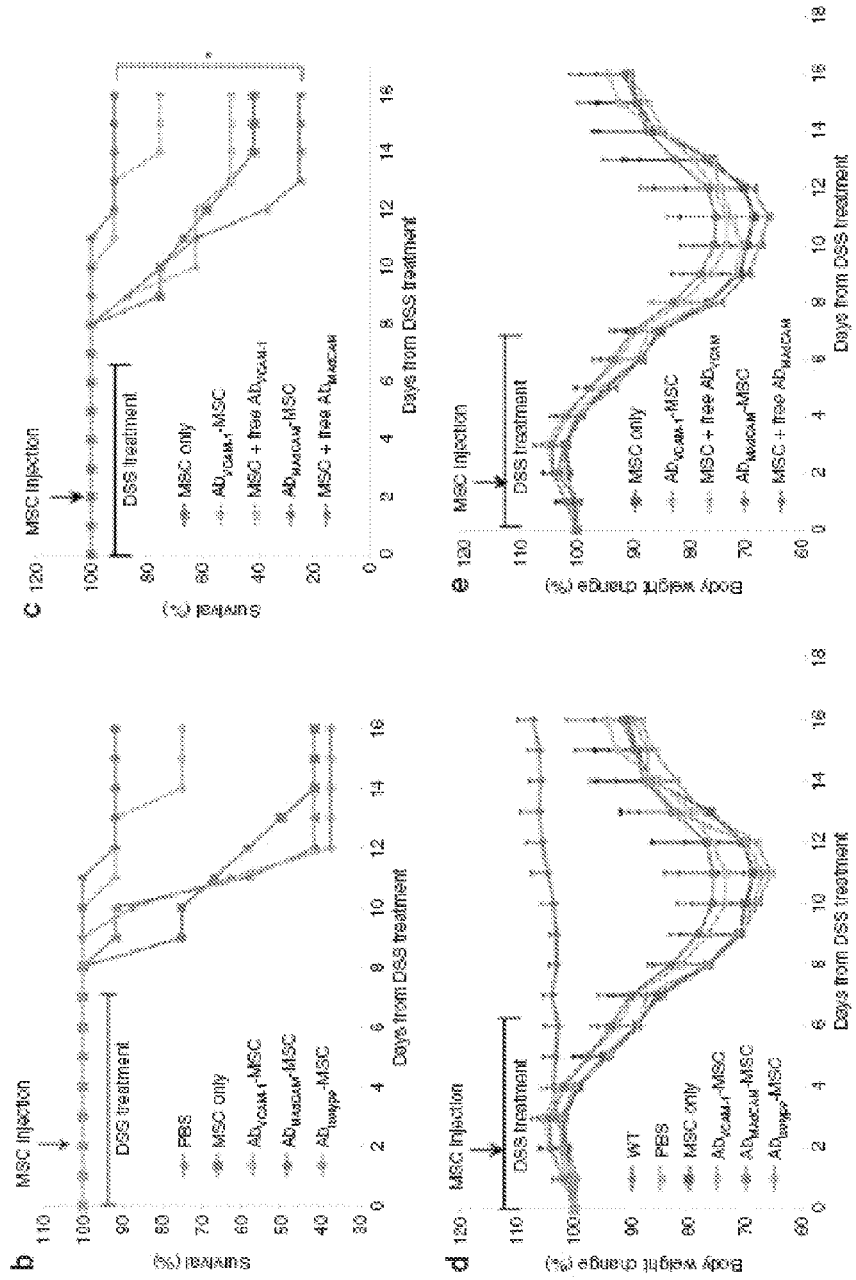
Figs. 3B-E

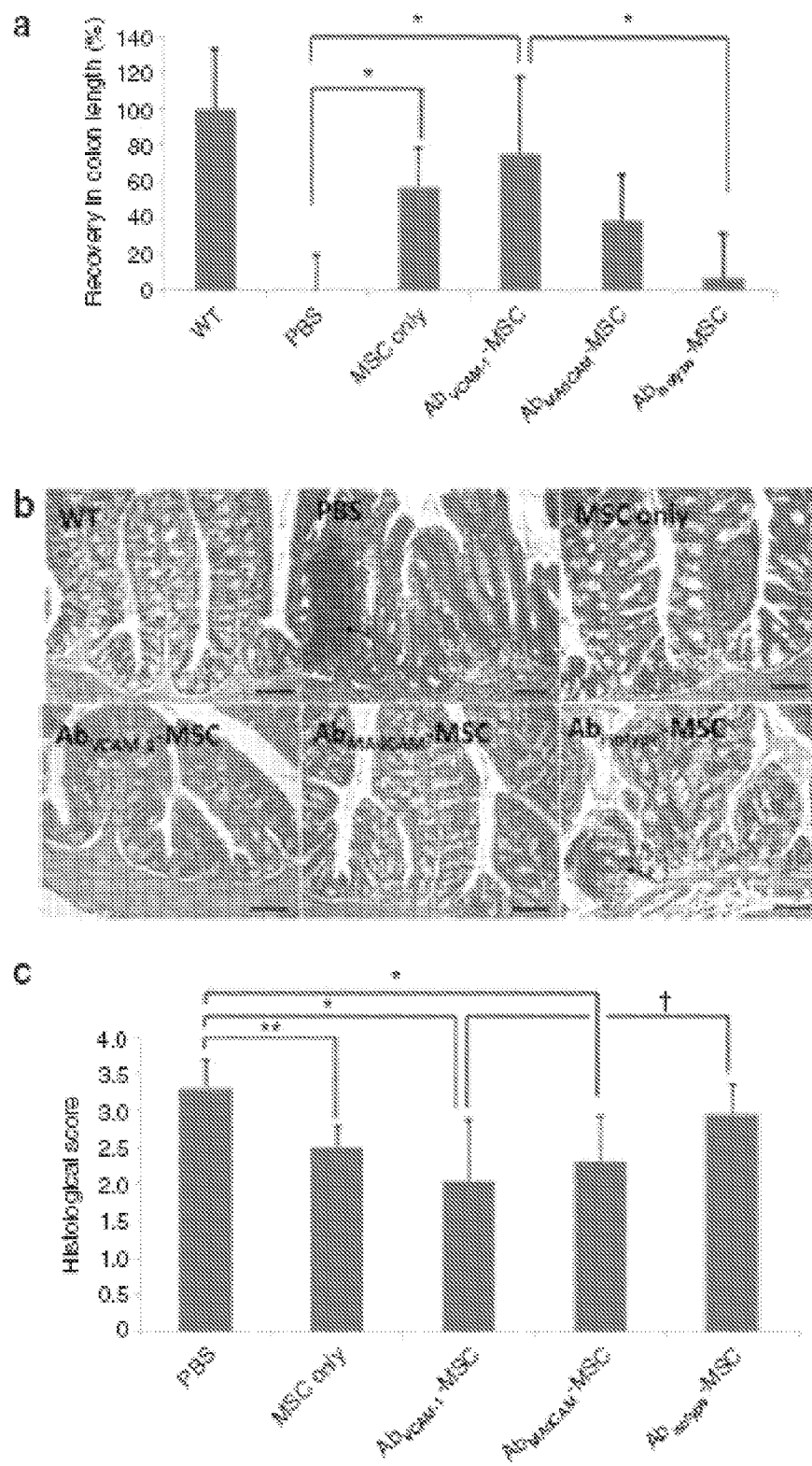
Fig. 4A-C

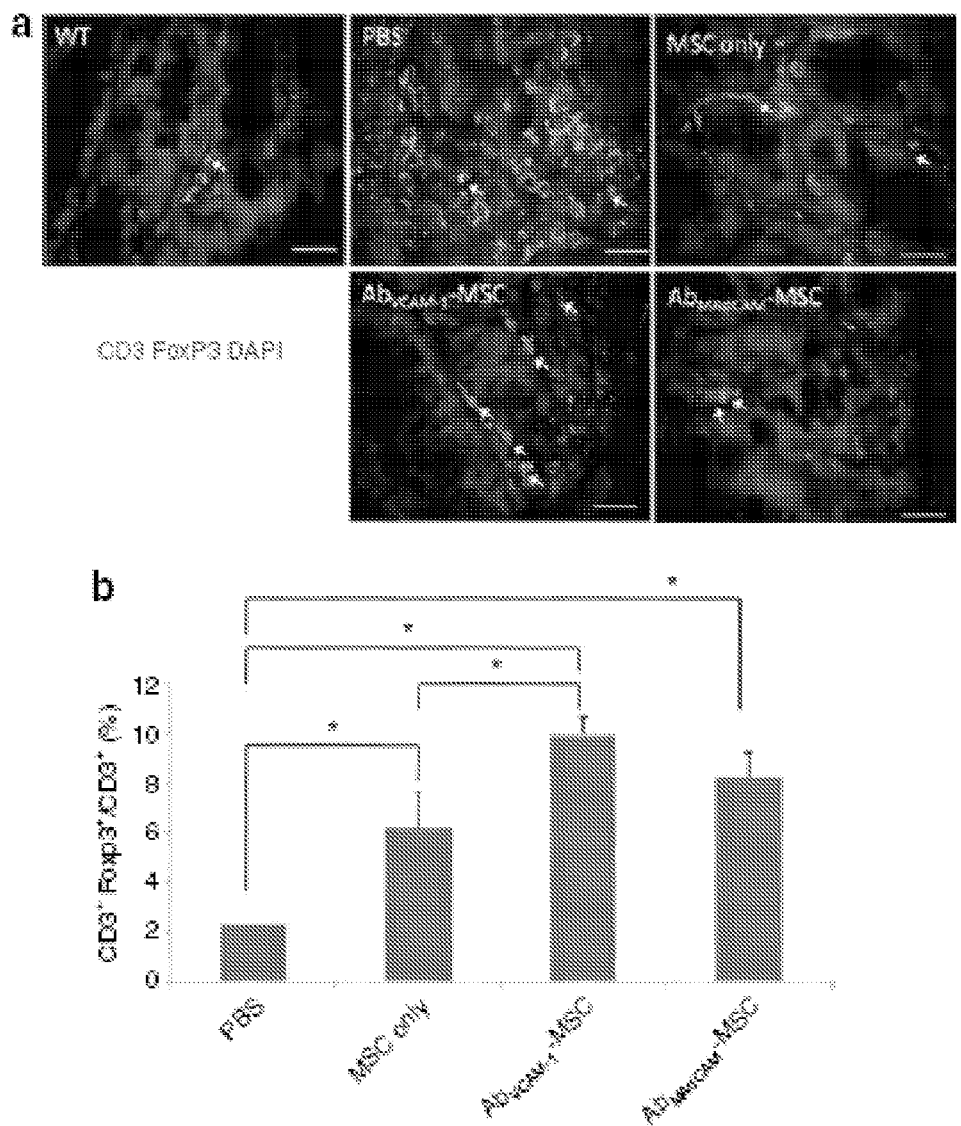
Figs. 5A-B

COMPOSITIONS AND METHODS OF TREATING INFLAMMATORY BOWEL DISEASE

RELATED APPLICATION

This application corres. to PCT/US2010/045613, filed Aug. 16, 2010, which claims priority from U.S. Provisional Application No. 61/233,910, filed Aug. 14, 2009, the subject matter which is incorporated herein by reference in their entirety.

TECHNICAL FIELD

This application generally relates to compositions and methods of treating inflammation and to compositions and methods of treating lymphocyte mediated inflammatory diseases.

BACKGROUND OF THE INVENTION

Various sources of mesenchymal stem cells (MSCs) have been tested as a treatment modality for inflammation-related diseases, such as inflammatory bowel disease (IBD), graft versus host disease, rheumatoid arthritis, type I diabetes, and multiple sclerosis. Newman et al. summarized that the mechanisms of action for the immunosuppressive effects observed in MSCs include both direct cellular contact, along with the secretion of soluble factors, such as transforming growth factor-$\beta$, prostaglandin E2, indoleamine-dioxygenase, nitric oxide, and tumor necrosis factor-a-stimulated gene-6 (Newman et al. (2009) Treatment of Inflammatory diseases with mesenchymal cells. *Inflamm Allergy Drug Targets* 8:110-123).

Recently, Ren et al. showed evidence that MSCs may arrest activated T cells in a graft versus host disease model via the secretion of proinflammatory factors and nitric oxide (Ren et al (2008). Mesenchymal stem cell-mediated immunosuppression occurs via concerted action of chemokines and nitric oxide. *Cell Stem Cell* 2:141-150). Additional evidence indicates that MSC immune-suppressive activity is localized at the sites of inflammation and regulated by cells and factors present in local microenvironment, indicating that greater MSCs homing and infusion close to inflamed sites may enhance therapeutic results.

SUMMARY

This application relates to a method of treating a lymphocyte mediated inflammation in a subject. The method includes administering a therapeutically effective amount of a cell delivery composition to the subject. The cell delivery composition includes an immunosuppressive cell and a plurality of targeting moieties that bind to endothelial cell adhesion molecules expressed by endothelial cells as a result of a lymphocyte mediated inflammatory response in the subject. The target moieties are coated on and linked to the immunosuppressive cell and enhance adherence of the immunosuppressive cell to an endothelial cell at a site of lymphocyte mediated inflammation when administered to the subject systemically. The cell delivery composition when administered to the subject suppresses lymphocyte mediated inflammation in the subject.

In some aspects of the application, the endothelial cell adhesion molecule can include an immunoglobulin superfamily cell adhesion molecule selected from the group consisting of ICAM1, ICAM2, ICAM3, VCAM1, and MAdCAM. The immunosuppressive cell can be a mesenchymal stem cell. The mesenchymal stem cell can include an allogeneic mesenchymal stem cell or an autologous mesenchymal stem cell.

In some aspects, the targeting moiety can include an antibody, such as a monoclonal antibody, a polyclonal antibody, or fragment thereof that binds to the endothelial cell adhesion molecule.

Another aspect of the application relates to a method of treating a T cell mediated inflammatory disease in a subject. The method includes administering a therapeutically effective amount of a cell delivery composition to the subject. The cell delivery composition includes an immunosuppressive cell and a plurality of targeting moieties that bind to endothelial cell adhesion molecules expressed by endothelial cells as a result of a T cell mediated inflammatory response in the subject. The target moieties are coated on and linked to the immunosuppressive cell and enhance adherence of the immunosuppressive cell to an endothelial cell at a site of the T cell mediated inflammation when administered to the subject systemically. The cell delivery composition when administered to the subject suppresses T-cell mediated inflammation associated with inflammatory disease in the subject.

In some aspects, the T cell mediated inflammatory disease can be selected from the group consisting of multiple sclerosis, uveitis, diabetes, and inflammatory bowel disease. In other aspects, the T cell mediated disease can be inflammatory bowel disease.

In some aspects of the invention, the endothelial cell adhesion molecule can include an immunoglobulin superfamily cell adhesion molecule selected from the group consisting of ICAM1, ICAM2, ICAM3, VCAM1, and MAdCAM. The immunosuppressive cell can be a mesenchymal stem cell. The mesenchymal stem cell can be an allogeneic mesenchymal stem cell or an autologous mesenchymal stem cell.

In some aspects, the targeting moiety includes at least one antibody, such as a monoclonal antibody, a polyclonal antibody, or fragment thereof that binds to the endothelial cell adhesion molecule.

Another aspect of the invention relates to a method of treating inflammatory bowel disease in a subject. The method includes administering a therapeutically effective amount of a cell delivery composition to the subject. The cell delivery composition includes an immunosuppressive cell and a plurality of targeting moieties that bind to endothelial cell adhesion molecules expressed by endothelial cells in the colon and small intestine of the subject. The target moieties are coated on and linked to the immunosuppressive cell and enhance adherence of the immunosuppressive cell to an endothelial cell at a site of the inflammation in the colon or small intestine when administered to the subject systemically. The cell delivery composition when administered to a subject suppresses inflammation in the colon and small intestine of the subject.

In some aspects of the invention, the endothelial cell adhesion molecule can include an immunoglobulin superfamily cell adhesion molecule selected from the group consisting of ICAM1, ICAM2, ICAM3, VCAM1, and MAdCAM. The immunosuppressive cell can be a mesenchymal stem cell. The mesenchymal stem cell can be an allogeneic mesenchymal stem cell or an autologous mesenchymal stem cell.

In some aspects, the targeting moiety can include an antibody, such as a monoclonal antibody, a polyclonal antibody, or fragment thereof that binds to the endothelial cell adhesion molecule.

BRIEF DESCRIPTION OF THE DRAWINGS

The foregoing and other features of the application will become apparent to those skilled in the art to which the application relates upon reading the following description with reference to the accompanying drawings, in which:

FIG. 1 illustrates immune cell suppression by MSC. (a) Phase contrast images of MSCs and splenocytes stimulated by CD3 antibody and cocultured in a 96-well microplate for 3 days. Arrows indicate colony formation in the splenocyte-only culture, indicating T-cell proliferation. Bar=200 μm. (b) Quantification of T-cell proliferation by 3H-thymidine uptake. The results show that T-cell suppression was MSC number dependent. Ab-coated MSCs showed greater T-cell suppression than MSCs only indicating a possible direct anti-VCAM-1 or anti-MAdCAM antibody effect. *P<0.01, **P<0.05 compared to MSC only. Data show mean±SD and are representative of two independent experiments. Ab, antibody; MSC, mesenchymal stem cell; PPG, palmitated protein G.

FIG. 4 illustrates colon length measurement and clinical scores of mice at day 16. (a) Colon length showed statistically improved recovery in MSCs only, AbVCAM-1-MSCs, $Ab_{MAdCAM}$-MSCs injected mice compared to PBS-injected mice; N=8-12, three independent experiments, ANOVA (P=0.001) with Tukey post hoc analysis. *indicates statistical significance at P<0.05. (b) H&E staining of paraffin-embedded sections of colon. Damages of crypts, severe infiltration by immune cells (arrow), and high-vascular density were found in PBS-mice and $Ab_{isotype}$-MSCs; Bar=100 μm. (c) Blinded histological scores of IBD levels based on H&E images; 0 indicates no damage, 4 indicates severe damage. AbVCAM-1-MSC-injected mice showed statistical significant improvement *P<0.01 versus PBS (*P<0.01), and versus $Ab_{isotype}$-MSCs (†P<0.05). MSC only injected mice were improved compared to PBS-injected (**P<0.05), as were $Ab_{MAdCAM}$-MSCs (*P<0.01). All comparisons were via Mann-Whitney testing. Ab, antibody; AbVCAM-1-MSCs, vascular cell adhesion molecule antibody-coated MSCs; ANOVA, analysis of variance; DSS, dextran sulfate sodium; H&E, hematoxylin and eosin; MSC, mesenchymal stem cell; PBS, phosphate-buffered saline.

FIG. 5 illustrates ratio of regulatory T cells (Treg) and total T cells in Ab-MSCmice. Paraffin-embedded colon sections were immunostained against CD3 (green, T cells), Foxp3 (red, Treg), and DAPI (nucleus). (a) Representative images of Treg are shown in each panel (arrows). Treg cells are doublestained with red fluorescence ($Foxp3^+$, intracellular marker) and blue staining (nucleus) surrounded by green fluorescence ($CD3^+$). (b) Ratio of Tregs to total T cells. The percentage of Treg cells compared to total T cells ($CD3^+$ $Foxp3^+$T cells/$CD3^+$T cells) is shown on the y-axis. $Ab_{VCAM-1}$-MSC-injected mice showed nearly five times greater percentage of Tregs compared to PBS-only (ANOVA, P<0.0001), whereas MSC only injected showed nearly a tripling of the Treg percentage compared to PBS-injected mice (P<0.05); ANOVA, analysis with Tukey post hoc analysis. Interestingly, $Ab_{VCAM-1}$-MSCs showed a statistical difference compared to PBS and MSC only (ANOVA, *P<0.05, Tukey's post hoc test). Ab, antibody; AbVCAM-1-MSCs, vascular cell adhesion molecule antibody-coated MSCs; ANOVA, analysis of variance; DAPI, 4'-6-diamidino-2-phenylindole; MSC, mesenchymal stem cell; PBS, phosphate-buffered saline.

DETAILED DESCRIPTION

Figure 2E:
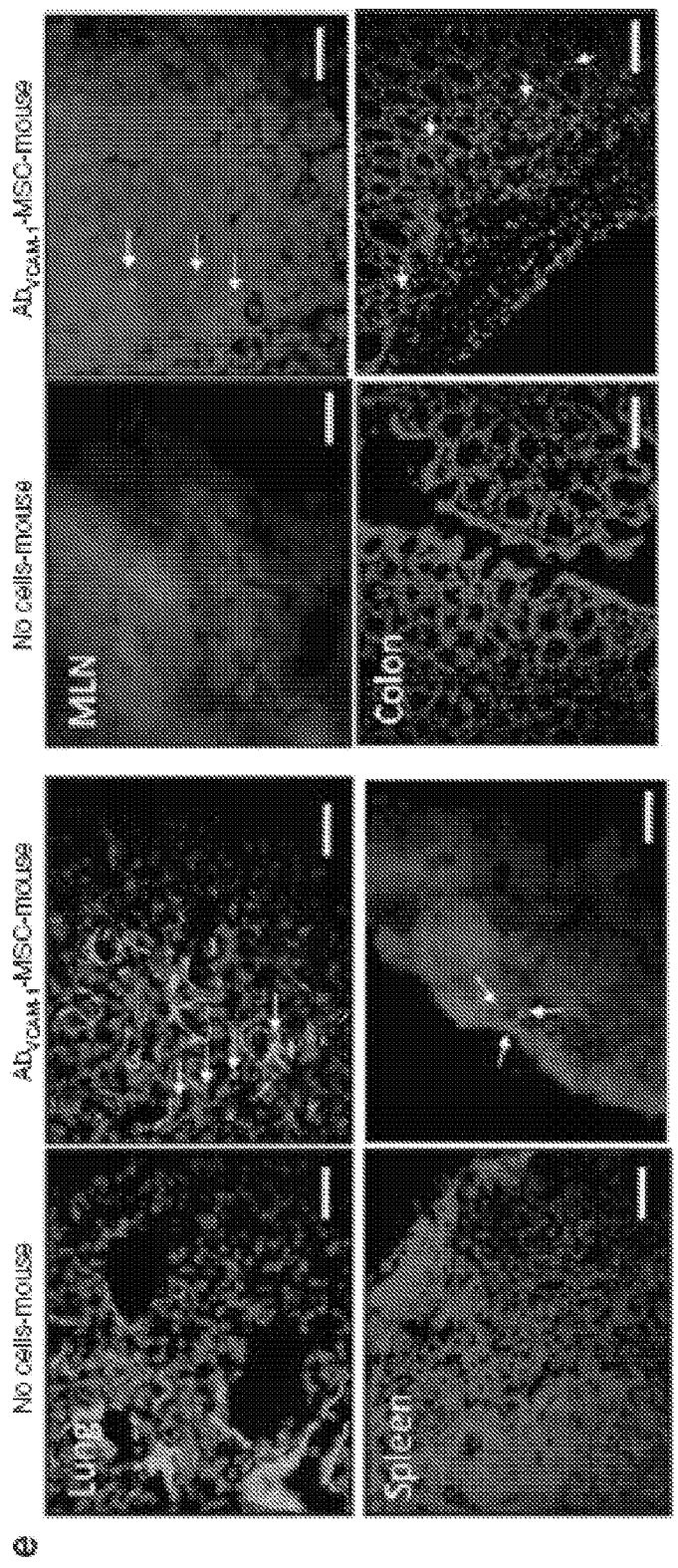
FIG. 2 illustrates in vivo bioluminescence imaging (BLI) of fluc-MSCs delivery. (a) Outline of experimental approach; mice were injected with $1.0 \times 10^6$ MSCs. (b) Representative BLI images. No signal was detected in mice without cell injection. $Ab_{VCAM-1}$-MSCs-injected mice showed the strongest signal among MSC only and $Ab_{MAdCAM}$-MSCs in MLN and colon. (c) Quantification of fluc-MSCs delivery to each organ. A statistically significant 1.8-fold increase by $Ab_{VCAM-1}$-MSCs relative to MSC only was demonstrated (n=10-12, 3-4 independent experiments, *P<0.02, Student's t-test). (d) Quantification of BLI for different organs comparing $Ab_{VCAM-1}$-MSCs to isotype Ab control. The signal from $Ab_{VCAM-1}$-MSCs in spleen, mesenteric lymph node (MLN), and colon was four-, three-, and twofold higher, respectively, than that of $Ab_{isotype}$-MSCs injected mice. *P<0.05, Student's t-test. Similar delivery efficiency of $Ab_{isotype}$-MSCs and $Ab_{VCAM-1}$-MSCs was found in the lung. (e) Ex vivo imaging of far-red dye labeled MSCs in lung, spleen, mesenteric lymph node (MLN), and colon. Arrows indicate MSCs in organs of $Ab_{VCAM-1}$-MSCs injected mouse. Green color is autofluorescent background staining which is easily distinguished from far-red dye labeled MSCs. Ab, antibody; AbVCAM-1-MSCs, vascular cell adhesion molecule antibody-coated MSCs; MSC, mesenchymal stem cell.

The practice of the application will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, $3^{rd}$ Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. By Bonifacino, Dasso, Lippincott-Schwartz, Harford, and Yamada, John Wiley and Sons, Inc., New York, 1999.

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

As used herein, the term "subject" refers to any warm-blooded organism including, but not limited to, human beings, rats, mice, dogs, goats, sheep, horses, monkeys, apes, rabbits, cattle, etc.

The term "or" is used herein to mean, and is used interchangeably with, the term "and/or," unless context clearly indicates otherwise.

The term "leukocyte" means white blood cell. Unlike red blood cells, white blood cells occur in many different types. Examples of leukocytes include granulocytes, neutrophils, eosinophils, basophils, lymphocytes, and monocytes.

The term "lymphocyte" as used herein refers to any of the mononuclear nonphagocytic leukocytes found in the blood, lymph, and lymphoid tissues which are derived from lymphoid stem cells; they comprise the body's immunocytes and their precursors (e.g., T cells, B cells and Natural Killer (NK) cells).

The term "T cell" (i.e., T lymphocytes) as used herein refers to a lymphocyte that matures in the thymus and expresses a T cell receptor, CD3, and CD4 or CD8. The term includes several distinct T cell subpopulations (e.g., Cytotoxic T cells (CTLs or $T_C$), T regulatory ($T_{reg}$) cells, T helper ($T_H$) cells, $T_{H1}$ cells and $T_{H2}$ cells). The term "T cell" is further intended to include all cells within the T cell lineage, including thymocytes, immature T cells, mature T cells and the like, from a mammal (e.g., human or mouse).

The term "T regulatory cell" or "$T_{reg}$ cell" as used herein refers to a type of T cell that carries CD4 on its surface and is distinguished from $T_H$ cells by surface markers, such as CD25, assocated with its stage of activation.

The term "immune response" includes any response associated with immunity including, but not limited to, increases or decreases in cytokine expression, production or secretion (e.g., IL-12, IL-10, TGF-β or TNFα expression, production or secretion), cytotoxicity, immune cell migration, antibody production and/or immune cellular responses. The term "immune response" may further include, but is not limited to a humoral response, a cell mediated immune response, an autoimmune response, a hyperimmune response, an inflammatory response, an innate response, an immune tolerance, and/or a hypersensitivity response.

The term "T cell mediated immune response" means an immune response in which T cells directly or indirectly mediate or otherwise contribute to an immune response in a mammal. The T cell mediated immune response may be associated with cell mediated effects, lymphokine mediated effects, etc., and even effects associated with B cells if the B cells are stimulated, for example, by the lymphokines secreted by T cells.

The terms "targeting", "homing", "migration", "localization" or "trafficking" refer to the trafficking patterns of cells (e.g., lymphocytes and/or the coated immunosuppressive cells of the application) mediated by unique combinations of cellular adhesion molecules and chemokines. For example, "homing" of an antibody coated immunosuppressive cell of the application is defined as the arrest or adherence of the cell within the vasculature of a tissue (e.g., an activated endothelial cell) and/or transmigration across the endothelium.

The term "autoimmune disease" refers to a spontaneous or induced malfunction of the immune system of mammals in which the immune system fails to distinguish between foreign immunogenic substances within the mammal and/or autologous ("self") substances and, as a result, treats autologous ("self") tissues and substances as if they were foreign and mounts an immune response against them. Autoimmune disease is characterized by production of either antibodies that react with self tissue, and/or the activation of immune effector T cells that are autoreactive to endogenous self antigens. Three main immunopathologic mechanisms act to mediate autoimmune diseases: 1) autoantibodies are directed against functional cellular receptors or other cell surface molecules, and either stimulate or inhibit specialized cellular function with or without destruction of cells or tissues; 2) autoantigen-autoantibody immune complexes form in intercellular fluids or in the general circulation and ultimately mediate tissue damage; and 3) lymphocytes produce tissue lesions by release of cytokines or by attracting other destructive inflammatory cell types to the lesions. These inflammatory cells in turn lead to production of lipid mediators and cytokines with associated inflammatory disease.

The term "inflammation" refers to both acute responses (i.e., responses in which the inflammatory processes are active) and chronic responses (i.e., responses marked by slow progression and formation of new connective tissue). Acute and chronic inflammation can be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

As used herein, the term "antibody" refers to whole antibodies, e.g., of any isotype (IgG, IgA, IgM, IgE, etc.), and includes fragments thereof which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term "antibody" also includes polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies. The term "diabodies" refers to dimeric scFvs. The components of diabodies typically have shorter peptide linkers than most scFvs and they show a preference for associating as dimers.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may comprise chains synthesized from engineered DNA sequences that have been modified by, for instance, substituting one amino acid for another to eliminate disulfide linkage sites. The fragment may also optionally be a multimolecular complex. A functional antibody fragment will typically comprise at least about 50 amino acids and more typically will comprise at least about 200 amino acids.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced.

The term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

The term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

The term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the term "homing peptide" refers to a particular peptide that binds relatively specifically to an epitope of a target tissue or organ, following administration to a subject. In general, a homing peptide that selectively homes to a target tissue is characterized, in part, by detecting at least a 2-fold greater specific binding of the peptide to the target tissue as compared to a control tissue.

The terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH2-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

As used herein, the terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" of Inflammatory Bowel Disease includes increasing healing at the disease site.

As used herein, the terms "effective," "effective amount," and "therapeutically effective amount" refer to that concentration or amount of antibody coated immunosuppressive cells described herein or pharmaceutical composition thereof that results in amelioration of symptoms or a prolongation of survival in a subject with a lymphocyte mediated inflammatory disease or related disorder. An "effective amount" of antibody coated immunosuppressive cells may be determined empirically. A therapeutically relevant effect relieves to some extent one or more symptoms of a lymphocyte mediated inflammatory disease or related disorder, or returns to normal either partially or completely one or more physiological or biochemical parameters associated with or causative of a lymphocyte mediated inflammatory disease or related disorder.

This application generally relates to compositions and methods of suppressing inflammation in a subject using cell-based therapies and particularly relates to methods of treating lymphocyte or T-cell mediated inflammation in the subject. The method can include administering a therapeutically effective amount of a cell delivery composition to the subject. The cell delivery composition of the application includes an immunosuppressive cell and a plurality of targeting moieties that bind to endothelial cell adhesion molecules expressed by endothelial cells as a result of an inflammatory response in the subject. It has been shown that the cell delivery composition, when administered to the subject, suppresses lymphocyte or T-cell mediated inflammation in the subject.

While not wishing to be bound to theory, it is expected that, the increased presence of the cell delivery composition locally at the site of lymphocyte or T-cell mediated inflammation can regulate and even ameliorate immune and inflammatory responses through contact-dependent and soluble factors Immunosuppressive cells of the cell delivery composition have been shown to have extensive potentials for inhibiting an immune response at a site of inflammation. For example, it is thought that immunosuppressive cells, such as mesenchymal stem cells (MSCs), produce a "quieting" effect on the inflammatory process owing to their immunosuppressive potential. It is contemplated that immunosuppressive cells act locally by secreting cytokines and through cell-to-cell interaction at the site of inflammation to inhibit the immune response and thus ameliorate immune related disease. Thus, a wide variety of diseases or injuries may be treated by delivering an immunosuppressive cell to a target diseased or injured/inflamed tissue so that the immune response is inhibited.

By way of example, a cell delivery composition comprising MSCs coated with an anti-CAM antibody ($Ab_{CAM}$) targeting moiety was administered in vivo to an experimental acute colitis mouse model of inflammatory bowel disease (IBD). In this IBD model, activated T cells promote macrophage activation and neutrophil infiltration, resulting in a transmural inflamed intestinal mucosa, characterized by prolonged and uncontrolled production of proinflammatory cytokines and chemokines. It was found that the $Ab_{CAM}$ antibody coated on and linked to MSCs increased cell delivery to inflamed colon, suppressed inflammation of the inflamed colon, and increased the efficacy of MSC treatment of IBD compared to controls.

In accordance with an aspect of the application, the immunosuppressive cell can include any immunosuppressive cell that either directly or indirectly reduces the activation or efficacy of a lymphocyte or T-cell mediated immune response at a site of inflammation in the subject. Examples of immunosuppressive cells that can be used in the cell delivery composition are MSCs, multipotent adult progenitor cells (MAPCs), regulatory T cells ($T_{regs}$), such as CD4$^+$FoxP3$^+$ $T_{reg}$ cells, Tr1, Th3, CD8$^+$CD28$^-$, and Qa-1 restricted CD8$^+$T cells. Naturally occurring, MSCs, MAPCs, and thymic-derived T regulatory cells are potent suppressors of adverse lymphocyte mediated immune responses. For example, preclinical studies have shown that either freshly isolated or ex vivo expanded $T_{reg}$ cells can prevent both local and systemic organ and tissue destruction. (See Riley et al. (2009) *Human T Regulatory Cell Therapy: Take a Billion or So and Call Me in the Morning*. Immunity 30:656-665).

In certain embodiments, the immunosuppressive cell is an MSC. MSCs include the formative pluripotent blast or embryonic cells that differentiate into the specific types of connective tissues, (i.e., the tissue of the body that support specialized elements, particularly including adipose, osseous, cartilaginous, elastic, muscular, and fibrous connective tissues depending on various in vivo or in vitro environmental influences.

MSCs for use with the application may be derived from any human or non-human tissue that provides mesenchymal stem cells capable of being immunosuppressive according to the methods disclosed herein. Examples of tissue sources include prenatal sources, postnatal sources, and combinations thereof. Tissues for deriving a suitable source of mesenchymal stem cells include, but are not limited to, bone marrow, blood (peripheral blood), dermis, periosteum, synovium, peripheral blood, skin, hair root, muscle, uterine endometrium, adipose, placenta, menstrual discharge, chorionic villus, amniotic fluid and umbilical cord blood and tissue. MSCs may be derived from these sources individually, or the sources may be combined to produce a mixed population of MSCs from different tissue sources.

Mesenchymal stem cell compositions for use with the application may comprise purified or non-purified MSCs. MSCs for use with the application include those disclosed in the following references, the disclosures of which are incorporated herein by reference: U.S. Pat. Nos. 5,215,927; 5,225,353; 5,262,334; 5,240,856; 5,486,359; 5,759,793; 5,827,735; 5,811,094; 5,736,396; 5,837,539; 5,837,670; 5,827,740; 6,087,113; 6,387,367; 7,060,494; Jaiswal et al., J. Cell Biochem. (1997) 64(2): 295 312; Cassiede et al., J. Bone Miner. Res. (1996) 11(9): 1264 1273; Johnstone et al., (1998) 238 (1): 265 272; Yoo, et al., J. Bone Joint Sure. Am. (1998) 80(12): 1745 1757; Gronthos, Blood (1994) 84(12): 416-44173; Basch et al., J. Immunol. Methods (1983) 56:269; Wysocki and Sato, Proc. Natl. Acad. Sci. (USA) (1978) 75: 2844; and Makino et al., J. Clin. Invest. (1999) 103(5): 697 705.

In some embodiments, the immunosuppressive cell can be a $T_{reg}$ cell. $T_{reg}$ cells suppress lymphocyte mediated immune responses and are regulated through the production of cytokines, including IL-10 and TGFβ. Animal studies have shown that $T_{regs}$ inhibit the development of autoimmune diseases such as experimentally induced inflammatory bowel disease, experimental allergic encephalitis, and autoimmune diabetes. Therefore, the application contemplates the ability to increase the immunosuppressive activity of regulatory T cell populations by increasing the delivery of these cells to sites of inflammation.

In other embodiments, the immunosuppressive cell is a multipotent adult progenitor cell. A MAPC is a non-embryonal stem (ES) cell, non-embryonal germ (EG) cell, non-germ cell that can give rise to cell lineages of more than one germ layer, such as all three germ layers (i.e., endoderm, mesoderm, and ectoderm). MAPCs also have telomerase activity. They may be positive for oct-3/4 (e.g., human oct-3A). They also may express one or more of rex-1, rox-1, sox-2, SSEA-4, and/or nanog. The term "adult" in MAPC is not restrictive. It only denotes that these cells are not ES, EG, or germ cells. MAPCs also have been referred to as multipotent adult stem cells (MASCs). See, for example, U.S. Pat. No. 7,015,037, which is herein incorporated by reference as to the methods disclosed therein for isolating and growing MAPCs/MASCs.

Additional immunosuppressive cells for use in the application can be identified using well known methods. For example, the measurement of the ability to inhibit immune reaction can be carried out by using a reaction system in which peripheral blood cells prepared from two or more different individuals are mixed (MLR) or a reaction system.

Immunosuppressive cells can be expanded ex vivo prior to use in the present method. For example, CD34+ MSCs can be derived from the bone marrow of a subject and then maintained in culture. "Cultured" and "maintained in culture" are interchangeably used when referring to the in vitro cultivation of cells and include the meaning of expansion or maintenance of a cell population under conditions known to be optimal for cell growth. The cell culture is maintained under culture conditions including suitable temperature, pH, nutrients, and proper growth factors, which favor the in vitro expansion and survival of the immunosuppressive cells. In certain embodiments, immunosuppressive cells may be harvested and stored (e.g., by cryogen freezing), allowing banking of cells for later use.

In some embodiments of the application, immunosuppressive cells are grown under conditions that incorporate the use of a culture media that comprises serum. The application may be practiced with serum from any mammal including, but not limited to, human, bovine, goat, pig, horse, rabbit, rat, and combinations thereof. The amount of serum used may vary according to the intended use of the stem cells being cultured. In some embodiments of the application, the immunosuppressive cells are grown in media comprising less than about 5% serum. Some embodiments of the application culture immunosuppressive cells in medium containing between about 0.1% and 0.2% serum.

The targeting moieties of the cell delivery composition are coated on and linked to the immunosuppressive cell and enhance adherence of the immunosuppressive cell to an endothelial cell at a site of lymphocyte or T-cell mediated inflammation when administered to the subject systemically. The targeting moiety can include any protein, peptide, antibody, antibody fragment, or small molecule includes any moiety capable of interacting with, complexing with, and/or binding to an endothelial cell adhesion molecule (CAM) that is expressed by an endothelial cells at a site of the lymphocyte and/or T-cell mediated inflammation.

Endothelial CAMs or cell adhesion proteins are, in general, the molecules that adhere cells to each other in the development and differentiation of individuals or in migration of cells to a local site, and are known to be essential molecules for organic and functional contacts in a living body. CAMs are roughly classified from their structural characteristics into five (5) families, immunoglobulin superfamily, integrin family, selectin family, cadherin family, and CD44 family.

In some embodiments, the endothelial CAM that the targeting moiety can interact with, complex with, and/or bind is a cell adhesion molecule of the immunoglobulin superfamily. Adhesion molecules belonging to immunoglobulin superfamily are characterized by the existence of repeated loop-like domains formed with disulfide bonds. Examples of immunoglobulin CAMs are intercellular adhesion molecule-1 "ICAM-1", vascular cell adhesion molecule-1 "VCAM-1" and mucosal addressin cell adhesion molecule-1 "MAdCAM-1".

In other embodiments, the endothelial CAM that the targeting moiety can interact with, complex with, and/or bind is an ICAM. ICAMs are members of the immunoglobulin superfamily that act as a cellular adhesion molecule that bind to integrins present on various leukocytes. These intercellular adhesion molecules are continuously present in low concentrations in the membranes of leukocytes and endothelial cells. Upon cytokine stimulation, the concentrations greatly increase. ICAMs employed by the application include ICAM-1, ICAM-2, and ICAM-3. ICAM-1 (also known as CD54) for example, can be induced by interleukin-1 (IL-1) and tumor necrosis factor alpha (TNFα) and is expressed by the vascular endothelium.

In other embodiments, the endothelial CAM that the targeting moiety can interact with, complex with, and/or bind is VCAM-1, also known as CD106. The VCAM-1 protein mediates the adhesion of lymphocytes, monocytes, eosinophils, and basophils to vascular endothelium. Upregulation of VCAM-1 in endothelial cells by cytokines occurs as a result of increased gene transcription (e.g., in response to tumor necrosis factor-alpha (TNF-α) and Interleukin-1 (IL-1)).

In still other embodiments, the endothelial CAM that the targeting moiety can interact with, complex with, and/or bind is MAdCAM-1. MAdCAM-1 is preferentially expressed on gut-associated endothelial cells and plays a central role in leukocyte homing to mucosal sites and inflamed endothelium tissues. MAdCAM-1 has also been found to be expressed on high endothelial venules (HEV) of both mesenteric lymph nodes and Peyers patches as well as on sinus-lining cells of the spleen. Similar to ICAM-1 and VCAM-1 expression, endothelial cell MAdCAM-1 gene expression is inducible with TNF-α and IL-1 cytokine activation.

Resting endothelium express low levels of endothelial CAMs (e.g., ICAM-1, VCAM-1). As an inflammatory response develops at a site of lymphocyte mediated inflammation, various cytokines, such as TNFα and other inflammatory mediators act on the local blood vessels, inducing increased expression of endothelial cell adhesion molecules (CAMs). The vascular endothelium is then said to be "activated", or inflamed.

It is therefore contemplated by the application that activated endothelium tissue will include endothelial cells expressing an increased number of endothelial CAMs compared to a resting endothelium. When endothelial cells become inflamed, endothelial CAMs become available on the surface of the cell allowing for their enhanced adherence with the targeting moiety coated immunosuppressive cells described herein to the site.

As one skilled in the art would appreciate, any site of lymphocyte mediated inflammation that is suitable for an immunosuppressive cell delivery may be employed, wherein a delivered coated immunosuppressive cell is capable of adhering to an endothelial CAM and reducing the activation or efficacy of the immune system at the site of lymphocyte mediated inflammation. In certain embodiments, the site of lymphocyte mediated inflammation can be selected from endothelium tissue, intestinal tissue, neuronal tissue (including both neuron and glia), connective tissue, hepatic tissue, pancreatic tissue, kidney tissue, bone marrow tissue, cardiac tissue, retinal tissue and lung tissue.

In some embodiments, the site of lymphocyte mediated inflammation is a high endothelial venule (HEV)-like structure found in tertiary extralymphoid chronic inflammatory disease sites (e.g., mucosal epithelia in gut, lungs, and genitourinary tracts, liver, brain and skin). These HEV like structures express several mucins including GlyCAM-1, MAdCAM-1 and CD34, that are normally displayed on normal HEVs. These HEV regions have been observed in a number of chronic inflammatory diseases in humans, including but not limited to rheumatoid arthritis, Crohn's disease, ulcerative colitis, Graves' disease, Hashimoto's thyroiditis, and diabetes mellitus.

In an aspect of the application, the targeting moiety can include antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((scFv)2 fragments), diabodies, tribodies or tetrabodies, which typically are covalently linked or otherwise stabilized (i.e., leucine zipper or helix stabilized) scFv fragments; and other targeting moieties include for example, homing peptides, fusion proteins, receptors, ligands, aptamers, and peptidomimetics.

In a particular embodiment, the targeting moiety can include a monoclonal antibody, a polyclonal antibody, and a humanized antibody. Such antibody can bind to an antigen of a target tissue and thus mediate the delivery of an immunosuppressive cell to the site of inflammation. For example, antibodies can be selected that are most likely to bind to a cell adhesion molecule described herein (e.g., a superfamily immunoglobulin CAM).

Such antibodies (e.g., an anti-CAM antibody or $Ab_{CAM}$) employed in the application can recognize cell adhesion molecules on cells at the site of inflammation (e.g., an inflamed endothelium) and adhere strongly enough so that they are not swept away by the flowing blood. In one example, an antibody of the application enables binding or adherence that is strong enough to resist the detachment of MSCs coated with the antibody from endothelial cells while under physiological flow (shear).

Therefore, in accordance with the application, the at least one antibody can include at least one anti-intercellular adhesion molecule. For example, the at least one antibody can include at least one anti-ICAM-1 antibody also known as anti-CD56, at least one anti-ICAM-2 antibody and/or at least one anti-ICAM-3 antibody. In certain embodiments, the at least one antibody can include anti-vascular cell adhesion molecule-1 (VCAM-1) antibodies also known as anti-CD106 antibodies. In certain embodiments, the at least one antibody can also include anti-mucosal addressin cell adhesion molecule-1 (MAdCAM-1) antibody.

In some embodiments, a combination of targeting antibody molecules is contemplated. One skilled in the art would recognize that a combination of antibodies can include any combination of antibodies that can bind to a corresponding number of CAMs on at a site of inflammation. For example, anti-VCAM-1 and anti-MAdCAM-1 antibodies can be bound to the same immunosuppressive cell and administered to a subject, wherein an activated endothelial cell at the site of inflammation expressed both VCAM-1 and MAdCAM-1. However, an immunosuppressive cell coated with multiple specificities of $Ab_{CAMs}$ is not limited to adhering to target cells that express each and every corresponding CAM, as one corresponding CAM may be sufficient for adherence in accordance with the application.

Preparation of antibodies may be accomplished by any number of well known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kindt, Goldsby, and Osborne, (2007) Kuby Immunology (6th Ed.), pp 105-106, W.H. Freeman and Company, New York, for a general overview of monoclonal antibody production, that portion of which is incorporated herein by reference).

Over the past several decades, antibody production has become extremely robust. In vitro methods that combine antibody recognition and phage display techniques allow one to amplify and select antibodies with very specific binding capabilities. See, for example, Holt et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. Binding epitopes may range in size from small organic compounds such as bromo uridine and phosphotyrosine to oligopeptides on the order of 7-9 amino acids in length.

In one embodiment, phage display technology may be used to generate an antibody specific for a desired cell adhesion molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-VL product (encoding a scFv fragment) is selected for and amplified by PCR. Restriction sites are introduced into the ends of the $V_H$ linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as fd and M13, typically M13.

In phage display vectors, the $V_H$ linker-VL sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (RPAS), commercially available from GE Healthcare Bio-Sciences Corp. of Piscataway, N.J. and the pSKAN Phagemid Display System, commercially available from Boca Scientific Inc. of Boca Raton, Fla. Phage display systems, their construction and screening methods are described in detail in, among others, U.S. Pat. Nos. 5,702,892, 5,750,373, 5,821,047 and 6,127,132, each of which are incorporated herein by reference in their entirety.

An antibody need not originate from a biological source. A targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule (e.g., a CAM), or a fragment or derivative thereof. Such immunogens may be isolated from a source where they are naturally occurring or may be synthesized using methods known in the art. For example, peptide chains may be synthesized by 1-ethyl-3-[dimethylaminopropyl]carbodiimide (EDC)-catalyzed condensation of amine and carboxyl groups. It certain embodiments, the immunogen may be linked to a carrier bead or protein. For example, the carrier may be a functionalized bead such as SASRIN® resin commercially available from Bachem Americas, Torrance, Calif. or a protein such as keyhole limpet hemocyanin (KLR) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random or semirandom polypeptide.

In certain embodiments, it may be desirable to mutate the binding region of a polypeptide antibody and select for an antibody with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may offer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan)

between the amino acids of targeting moiety. In exemplary embodiments, such modifications increase the protease resistance of a targeting moiety without affecting the activity or specificity of the interaction with a desired target molecule.

In certain embodiments, the antibodies or variants thereof may be modified to make them less immunogenic when administered to a subject. For example, if the subject is human, the antibody may be "humanized"; where the complimentarity determining region(s) of the hybridoma-derived antibody has been transplanted into a human monoclonal antibody, for example as described in Jones, P. et al. (1986), Nature, 321, 522-525 or Tempest et al (1991), Biotechnology, 9:266-273. Also, transgenic mice, or other mammals, may be used to express humanized antibodies. Such humanization may be partial or complete.

In certain embodiments, a targeting moiety of the application may comprise a homing peptide which selectively directs an immunosuppressive cell to a site of lymphocyte mediated inflammation. For example, a targeting moiety may comprise a homing peptide which selectively directs an immunosuppressive cell to an activated mucosal endothelium tissue.

Homing peptides for a target tissue (or organ) can be identified using various methods well known in the art. An exemplary method is the in vivo phage display method. Specifically, random peptide sequences are expressed as fusion peptides with the surface proteins of phage, and this library of random peptides are infused into the systemic circulation. After infusion into host mice, target tissues or organs are harvested, the phage is then isolated and expanded, and the injection procedure repeated two more times. Each round of injection includes, by default, a negative selection component; as the injected virus has the opportunity to either randomly bind to tissues, or to specifically bind to non-target tissues. Virus sequences that specifically bind to non-target tissues will be quickly eliminated by the selection process, while the number of non-specific binding phage diminishes with each round of selection. Many laboratories have identified the homing peptides that are selective for vasculature of brain, kidney, lung, skin, pancreas, intestine, uterus, adrenal gland, retina, muscle, prostate, or tumors. See, for example, Samoylova et al., 1999, *Muscle Nerve*, 22:460; Pasqualini et al., 1996, *Nature*, 380:364; Koivunen et al., 1995, *Biotechnology*, 13:265; Pasqualini et al., 1995, *J. Cell Biol.*, 130: 1189; Pasqualini et al., 1996, *Mole. Psych.*, 1:421,423; Rajotte et al., 1998, *J. Clin. Invest.*, 102:430; Rajotte et al., 1999, *J. Biol. Chem.*, 274:11593. See, also, U.S. Pat. Nos. 5,622,699; 6,068,829; 6,174,687; 6,180,084; 6,232,287; 6,296,832; 6,303,573; 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, *Meth. Enzymol.*, 217:228-257, Scott et al., *Science*, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or to cell surface receptors (see, e.g., Smith et al., 1993, *Meth. Enzymol.*, 217:228-257). For example, in vitro screening of phage peptide display libraries has been used to identify novel peptides that specifically bind to integrin adhesion receptors (see, e.g., Koivunen et al., 1994, *J. Cell Biol.* 124:373-380), and to the human urokinase receptor (Goodson et al., 1994, *Proc. Natl. Acad. Sci.*, USA 91:7129-7133). However, such in vitro studies provide no insight as to whether a peptide that can specifically bind to a selected receptor in vitro also will bind the receptor in vivo or whether the binding peptide or the receptor are unique to a specific tissue or organ in the body.

In certain embodiments, a targeting moiety of the application may be a fusion protein. Such fusion protein may contain a tag that facilitates its isolation, immobilization, identification, or detection and/or which increases its solubility. In a preferred embodiment, the fusion protein comprises an Fc fragment of antibodies. The Fc fragment can bind to a Protein A or Protein G. In another preferred embodiment, the fusion protein comprises a homing peptide which selectively directs an immunosuppressive cell to a site of lymphocyte mediated inflammation. An exemplary fusion protein comprises a homing peptide fused to the amino terminus of the Fc region of the human IgG sequence and to the carboxyl terminus of the oncostatin-M signal peptide. The fusion protein may contain other tags, for example, glutathione Stransferase (GST), calmodulin-binding peptide, thioredoxin, maltose binding protein, HA, myc, poly arginine, poly His, poly His-Asp or FLAG tags. Additional exemplary tags include polypeptides that alter protein localization in vivo, such as signal peptides, type III secretion system-targeting peptides, transcytosis domains, nuclear localization signals, etc. In various embodiments, a targeting moiety of the application may comprise one or more tags, including multiple copies of the same tag or two or more different tags. It is also within the scope of the application to include a spacer (such as a polypeptide sequence or a chemical moiety) between a targeting moiety of the application and the tag in order to facilitate construction or to optimize its structural constraints. In another embodiment, the tagged moiety may be constructed so as to contain protease cleavage sites between the tag and the moiety in order to remove the tag. Examples of suitable endoproteases for removal of a tag, include, for example, Factor Xa and TEV proteases.

In certain embodiments, the targeting moiety may comprise a receptor molecule, including, for example, receptors which naturally recognize a specific desired molecule of an activated endothelium tissue. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, *J. Molecular Recognition*, 13: 167-187). A preferred receptor is a chemokine receptor. Exemplary chemokine receptors have been described in, for example, Lapidot et al., 2002, *Exp Hematol*, 30:973-81 and Onuffer et al., 2002, *Trends Pharmacol Sci*, 23:459-67.

In other embodiments, the targeting moiety may comprise a ligand molecule, including, for example, ligands which naturally recognize a specific desired receptor of a target tissue (e.g., an endothelial CAM). Such ligand molecules include ligands that have been modified to increase their specificity of interaction with a target receptor, ligands that have been modified to interact with a desired receptor not naturally recognized by the ligand, and fragments of such ligands.

In still other embodiments, the targeting moiety may comprise an aptamer. Aptamers are oligonucleotides that are selected to bind specifically to a desired molecular structure of the target tissue. Aptamers typically are the products of an affinity selection process similar to the affinity selection of phage display (also known as in vitro molecular evolution). The process involves performing several tandem iterations of affinity separation, e.g., using a solid support to which the desired immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein which is involved in binding other proteins, peptidomimetic compounds can be generated which mimic those residues which facilitate the interaction. Such mimetics may then be used as a targeting moiety to deliver a progenitor cell to a target tissue. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al., 1986, *J Med Chem* 29:295; and Ewenson et al. in *Peptides: Structure and Function* (Proceedings of the 9th American Peptide Symposium) Pierce Chemical Co. Rockland, Ill., 1985), b-turn dipeptide cores (Nagai et al., 1985, *Tetrahedron Lett* 26:647; and Sato et al., 1986, *J Chem Soc Perkin Trans* 1:1231), and β-aminoalcohols (Gordon et al., 1985, *Biochem Biophys Res Commun* 126:419; and Dann et al., 1986, *Biochem Biophys Res Commun* 134:71).

Immunosuppressive cell of the application can be coated with a targeting moiety in one step or two step processes. In a one step process a targeting moiety can be directly linked to the immunosuppressive cell. In a two step process a targeting moiety of the application may be indirectly associated with an immunosuppressive cell. Indirect attachment may be achieved, for example, by providing a linker that associates with the immunosuppressive cell to be coated and with the targeting moiety. For example, the extracellular membrane of a cell can be coated with Protein G and then a monoclonal antibody can be joined with Protein G.

In certain embodiments, a targeting moiety of the application may be directly associated with an immunosuppressive cell. In some embodiments, this may be achieved, by modifying a targeting moiety with a lipophilic moiety to allow insertion into or association with the cell membrane. For example, methods for inserting a palmitated antibody into a cell membrane are described, for example, in Colsky and Peacock, *J Immunol Methods,* (1989) 124:179-87, incorporated herein by reference. Direct attachment to a cell may also be achieved by covalently attaching the antibody to another element that has an affinity for a marker on the surface of the immunosuppressive cell to be coated, such as an extracellular protein or oligosaccharide.

In other embodiments, a targeting moiety of the application may be indirectly associated with an immunosuppressive cell. Indirect attachment may be achieved, for example, by providing a linker that associates with the immunosuppressive cell to be coated and with the targeting moiety. Exemplary linkers include Protein G. Protein G is a highly stable surface receptor from Streptococcus sp. (Lancefield Group G), that has four Fe-fragment binding sites for immunoglobulins and each molecule can bind 2 molecules of IgG (See Reis, K. J., Ayoub, E. M., and Boyle, M. D. P. (1985) "A rapid method for the isolation and characterization of a homogenous population of streptococcal Fc receptors," J. Microbio. Methods 4:45-58; Bjorck, L. and Kronvall, G. (1984) "Purification and some properties of streptococcal protein G, a novel IgG-binding reagent," J. Immunol. 133:969-974; and European Patent Application No. 0131142, published on Jan. 16, 1985. The application concerns the use of proteolytic enzymes, e.g., papain, trypsin and pepsin, to solubilize the protein G bound to the streptococcal cell wall. The EPO application also discloses U.S. Pat. No. 3,850,798 which uses trypsin to recover protein A.)

Another exemplary linker is Protein A, which also binds Fc fragments, but with a different range of specificities. Linkers may be modified to associate with an immunosuppressive cell through any of the various approaches described above with respect to direct attachment of a targeting moiety. For example, the linker may be modified with a lipophilic moiety.

In certain exemplary embodiments, the linker is palmitated protein G (PPG) or palmitated protein A (PPA). There are a wide range of lipophilic moieties with which linkers or targeting moieties may be derivatived, including without limitation, palmitoyl moiety, myristoyl moiety, margaroyl moiety, stearoyl moiety, arachidoyl moiety, acetyl moiety, butytyl moiety, hexanoyl moiety, octanoyl moiety, decanoyl moiety, lauroyl moiety, palmitoleoyl moiety, behenoyl moiety, and lignoceroyl moiety. Preferred lipophilic moieties include palmitoyl moiety, myristoyl moiety, and margaroyl moiety.

In one specific embodiment, the linker is PPG. For example, MSCs are incubated with 50 µg/ml of palmitated protein G (PPG). The PPG-coated cells are then incubated in anti-VCAM-1 antibody and/or MAdCAM-1 at 100 ug/ml in growth medium for 1 hour and then washed to remove unreacted antibody.

A lipophilic group employed in the application can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1-C18)-alkyl phosphate diesters, —O—$CH_2$—CH(OH)—O—(C12-C18)-alkyl, conjugates with pyrene derivatives, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Optionally, the lipophilic moiety can be a lipophilic dye suitable for use in the application include, but are not limited to, diphenylhexatriene, Nile Red, Nphenyl-1 naphthylamine, Prodan, Laurodan, Pyrene, Perylene, rhodamine, rhodamine B, tetramethylrhodamine, Texas Red, sulforhodamine, 1,1'-didodecyl3,3,3', 3'tetra-methylindocarbocyanine perchlorate, octadecyl rhodamine B and the BODIPY® lipid dyes available from Molecular Probes Inc., Eugene, Oreg. Other exemplary lipophilic moieties include aliphatic carbonyl radical groups such as decanoyl, dodecanoyl, dodecenoyl, tetradecadienoyl, decynoyl or dodecynoyl.

Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive crosslinkers. Disuccinimidyl suberate (DSS), bismaleimidohexane (BMH) and dimethylpimelimidate, 2 HCL (DMP) are examples of useful homobifunctional cross-linking agents, and bis-[B-(4-azidosalicylamido)ethyl]disulfide (BASED) and Nsuccinimidyl-6(4'-azido-2'-nitrophenyl-amino)hexanoate (SANPAH) are examples of useful photoreactive cross-linkers for use in this application. For a review of protein coupling techniques, see Brinkley et al (1992), *Bioconjugate Chemistry*, 3(1):2-13, incorporated by reference herein.

One particularly useful class of heterobifunctional cross-linkers, included above, contains the primary amine reactive group, N-hydroxysuccinimide (NBS), or its water soluble analog N hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

In certain embodiments, the lipophilic moiety employed is a lipid moiety. Generally, a "lipid" is a member of a heterogeneous class of hydrophobic substances characterized by a variable solubility in organic solvents and insolubility, for the most part, in water. The principal class of lipids that are encompassed within this application are fatty acids and sterols (e.g., cholesterol). Derivatized proteins of the application contain fatty acids which are cyclic, acyclic (i.e., straight chain), saturated or unsaturated, mono-carboxylic acids. Exemplary saturated fatty acids have the generic formula: $CH_3(CH_2)nCOOH$.

In accordance with another aspect of the application it has been shown that reduced inflammation by immunosuppressive activity, in some instances, is associated with downregulation of the production of a wide panel of inflammatory/cytotoxic mediators by mucosal immune cells, and by increased levels of the anti-inflammatory cytokine IL-10. Therefore, in some embodiments, the immunosuppressive cell of the cell delivery composition can be transduced with modulatory cytokines, such as IL-10 in combination with being coated with a targeting moiety. In certain aspects the cell is transduced prior to coating the cell with a plurality of targeting moieties.

Any method of transducing mammalian cells known to the skilled artisan may be employed in the application. Viruses are commonly used as vehicles to deliver transgenes into stem cells that can be available to effectively infect dividing or nondividing cells. Integrating virus, including retrovirus or lentivirus, can insert their viral DNA into the host genomic DNA, which allows for stable genetic modification for the life of the host cells. Alternatively, nonintegrating viruses, including adenovirus or herpes saimirii virus, are preferentially used to obtain the expression of a therapeutic gene in an immunosuppressive cell of the application. In some embodiments, nonviral methods may be employed to transduce an immunosuppressive cell of a cell delivery composition with modulatory cytokines. Exemplary nonviral systems used for gene transfer include, but are not limited to liposome-based methods, electroporation, microporation and calcium phosphate techniques.

It is further contemplated by the application that the cell delivery composition of the application can also act as a drug delivery vehicle. For example, an immunosuppressive cell can be coated with an targeting moiety in combination with additional therapeutic antibodies, such as anti-tumor necrosis factor-a (e.g., INFLIXIMAB ETANERCEPT, or ADALIMUMAB), an anti-α4 Ab (e.g., NATALIZUMAB) or an anti-CD3 antibody (ORTHOCLONE OKT3).

In certain aspects, the application provides methods of administering a therapeutically effective amount of the cell delivery composition to a subject. The immunosuppressive cell having been either directly or indirectly complexed with a plurality of targeting moieties (e.g., a plurality of $Ab_{CAM}$ antibodies) can be administered to a subject by a variety of means. In some embodiments, the cell delivery composition can be administered to the subject systemically. In certain embodiments, the cell delivery composition can be delivered to the subject by intravenous injection into blood.

While the cell delivery composition of the application enhances adherence of an immunosuppressive cell to an endothelial cell at a site of lymphocyte or T-cell mediated inflammation when administered to the subject systemically, the cell delivery composition is not limited to systemic administration. Therefore, in other embodiments, the cell delivery composition can delivered to the subject by injection into or to an area proximate the site of inflammation. In still other embodiments, the cell delivery composition can be delivered to the subject by surgical implantation. In still other embodiments, the cell delivery composition is delivered to the subject by subcutaneous injection, intra-peritoneal injection, or intra-synovial injection.

In certain embodiments, the cell delivery composition may be inserted into a delivery device which facilitates introduction by injection or implantation into the subjects. Such delivery devices may include tubes or intraluminal devices, e.g., catheters, for injecting cells and fluids into the body of a recipient subject. In a preferred embodiment, the tubes additionally have a needle, e.g., a syringe, through which the cells of the application can be introduced into the subject at a desired location.

Cell delivery compositions may be prepared for delivery in a variety of different forms. For example, the coated cells may be suspended in a solution or gel or embedded in a support matrix when contained in such a delivery device. Coated cells may be mixed with a pharmaceutically acceptable carrier or diluent in which the progenitor cells of the application remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the application may be prepared by incorporating cells as described herein in a pharmaceutically acceptable carrier or diluent and, as required, other ingredients enumerated above, followed by filtered sterilization.

The cell delivery compositions of the application can be used to prevent local and systemic organ and tissue destruction in cell therapies aimed at alleviating T cell mediated diseases. Therefore, in certain aspects of the application, a method of adoptive immunosuppressive cell therapy is provided. According to the method, a therapeutically effective amount of cell delivery composition can be administered to the subject for the treatment of T cell mediated inflammatory diseases.

The term "T cell mediated inflammatory disease" refers to diseases and disorders in which an aberrant immune reaction involves T cell-mediated immune/inflammatory mechanisms, as opposed to humoral immune mechanisms. Thus, in certain embodiments, methods of the application pertain to treatments of immune disorders in which tissue destruction is primarily mediated through activated T cells and immune cells other than B-lymphocytes.

For example, the methods of the application can be used in the treatment of autoimmune conditions or diseases such as inflammatory diseases (for example rheumatoid arthritis, uveitis, inflammatory bowel disease (IBD), asthma, glomerulonephritis, lung fibrosis, Wegener's granulomatosis; chronic obstructive pulmonary disease (COPD); acute respiratory distress syndrome (ARDS); transfusion-related acute lung injury (TRALI); ischemia/reperfusion acute lung injury; and Goodpasture's disease), granulocytopenia, multiple sclerosis, myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD) and Alzheimer's disease (AD), psoriasis, hypersensitivity reactions of the skin, sepsis, atherosclerosis, ischemia-reperfusion injury, myocardial infarction, restenosis, vasculitis, systemic lupus erythematosus (SLE), and insulin-dependent diabetes. The methods of the application can also be used for the prevention or treatment of the acute rejection of transplanted organs where administration of a therapeutic described herein, may occur during the acute period following transplantation or as long-term post transplantation therapy.

In some embodiments of the application, the T cell mediated inflammatory disease or related disorders include chronic inflammatory diseases. Chronic inflammation develops when antigen persists. Chronic inflammation results in tissue damage and occurs in a large number of autoimmune diseases in which self antigens continually activate T cells. Chronic inflammatory diseases such as inflammatory bowel disease, rheumatoid arthritis, and asthma are commonly characterized by an abundant leukocyte infiltration in the affected tissue.

In certain embodiments, T cell mediated inflammatory diseases contemplated by the application include T cell mediated autoimmune diseases or disorders. The language "autoimmune disorder" is intended to include disorders in which the immune system of a subject reacts to autoantigens, such that significant tissue or cell destruction occurs in the subject. The term "autoantigen" is intended to include any antigen of a subject that is recognized by the immune system of the subject. The terms "autoantigen" and "self-antigen" are used interchangeably herein. The term "self" as used herein is intended to mean any component of a subject and includes molecules, cells, and organs. Autoantigens may be peptides, nucleic acids, or other biological substances.

Even though the methods of the application are intended for treatment of immune disorders mediated by cells other than B cells, the immune disorders may include autoimmune diseases and disorders characterized by the presence of autoantibodies. For example, multiple sclerosis, a T cell mediated autoimmune disorder, which can be treated by a method of the application, is frequently associated with the presence of autoantibodies to components of the central nervous system, such as myelin basic protein. Non limiting examples of T cell mediated autoimmune disorders that can be treated by the methods of the application include multiple sclerosis, EAE, diabetes type I, oophoritis, and thyroiditis.

Inflammatory bowel disease (IBD), including Crohn's disease and ulcerative colitis, is an autoimmune disease characterized by dysfunction of mucosal T cells and altered cellular inflammation that ultimately leads to damage of the distal small intestine and the colonic mucosa. As described above, it has been demonstrated that immunosuppressive cells play an important role in reducing inflammation related to (IBD).

Therefore, an exemplary embodiment of the application includes a method of treating inflammatory bowel disease in a subject. The method includes administering a therapeutically effective amount of a cell delivery composition to the subject, the cell delivery composition comprising an immunosuppressive cell and a plurality of targeting moieties that bind to endothelial cell adhesion molecules expressed by endothelial cells in the colon and small intestine of the subject. The targeting moieties being coated on and linked to the immunosuppressive cell and enhancing adherence of the immunosuppressive cell to an endothelial cell in the colon and small intestine of the subject when administered to the subject systemically, wherein the cell delivery composition suppresses inflammation in the colon and small intestine of the subject.

In some aspects of the application, the lymphocyte mediated inflammatory response and related disorders can include a natural killer (NK) cell mediated inflammatory response. NK cells have been shown to have a role in human inflammatory diseases including atopy, asthma and autoimmunity. It is most likely that the role of NK cells in these diseases is a function of their cytokine production. For example, in multiple sclerosis, cytokine production by NK cells correlates with disease activity. When NK cells are producing IFN-γ, patients are more likely to have active disease.

A therapeutically effective amount of cell delivery composition to be administered to a subject can be determined by a practitioner based upon such factors as the age of the subject and/or donor, the mode of administration, and/or the particular lymphocyte mediated inflammatory disease to be treated. In an exemplary embodiment, a therapeutically effective amount of cell delivery composition for the treatment of IBD is the amount or concentration of cells resulting in a significantly increased subject survival rate, increased body weight, improved histological scoring, increased IBD therapeutic score, reduced colon length and/or an increase in $T_{reg}$ cells in the colon of the subject. In some embodiments the number of coated immunosuppressive cells administered is from about $10^5$ to about $10^8$ cells.

Immune incompatibility includes cases where cells, preferably human cells from another subject (allogeneic cells), are introduced into a subject which are not compatible with the subject's immune system and thus are attacked and rejected by the subject's immune system, such as in organ rejection Immune incompatibilities also include cases where immune system cells are introduced into a subject, preferably from another subject, which are not compatible with the subject's cells and thus the introduced immune cells attack the subject's cells, such as in graft versus host disease.

Thus, in one embodiment, the subject has or is at risk for having graft versus host disease (GVHD). GVHD may be acute or it may be chronic. In another embodiment, the subject has or is at risk for graft rejection. In other embodiments, the subject is a recipient of a transplant, such as a solid organ transplant. Solid organ transplants include lung, heart, kidney, liver and skin transplants. Alternatively, the transplant may be a hematopoietic stem cell transplant, such as one from an unrelated donor. The transplant may also comprise umbilical vein hematopoietic stem cells, or peripheral blood stem cells. The transplants described herein can be HLA matched or HLA-unmatched. In some embodiments, the transplants described herein are allogeneic transplants.

The application additionally provides methods of preventing or reducing immune incompatibility in a subject in need thereof, the method comprising administering to the subject a therapeutically effective amount of cell delivery composition described herein. In one embodiment, the subject has or is at risk for having graft versus host disease (GVHD). The methods described herein to treat or prevent GVHD may be applied to acute and to chronic GVHD. Acute GVHD typically occurs within the first three months following a transplant. Chronic GVHD occurs two or three months after a transplant and may include symptoms similar to autoimmune diseases and rashes, and may include liver, stomach and intestinal problems.

The methods of the application are suitable for the prevention and treatment of GVHD in the course of bone marrow transplantation in patients suffering from diseases curable by bone marrow transplantation, including leukemias, such as acute lymphoblastic leukemia (ALL), acute nonlymphoblastic leukemia (ANLL), acute myelocytic leukemia (AML) and chronic myelocytic leukemia (CML), severe combined immunodeficiency syndromes (SCID), osteopetrosis, aplastic anemia, Gaucher's disease, thalassemia and other congenital or genetically-determined hematopoietic or metabolic abnormalities. The need for a bone marrow stem cell transplant arises because the only treatment that appears to have a chance of killing the disease in the host also kills the host's cellular immune system. Thus, the patient or host is treated to kill the target disease, and as a result of such treatment, the host's cellular immune system is also killed. Common methods of treatment include radiation treatment and chemotherapy, either alone or together, with or without accompanying surgery.

After such treatment, it is necessary to provide the patient with a means for regenerating the patient's immune system. The bone marrow or bone marrow hematopoietic stem cell transplant provides the basis for this immune system regeneration. The donor is treated to enrich his or her blood with bone marrow stem cells. The donor's blood is drawn and is centrifuged to separate the white blood cells, which include the desired stem cells necessary to regenerate the host's immune system from the rest of the blood. The separated white blood cells will also include the donor's T-cells. The separated white blood cells from the transplant inoculum are then infused into the host. After infusion into the host, the infused or transplanted stem cells will seed the host's bone marrow and will differentiate into different blood cell types. This regeneration of the immune system, i.e., the production by the host of T-cells which can attack aberrant cells, such as infected cells, takes several weeks to several months The methods described herein for treating or preventing GVHD are in some embodiments used in combination with other treatments. In one embodiment, a patient suffering or at risk of developing chronic GVHD can be treated with steroids such as cyclosporine, prednisone, and ozothioprine, or with cyclosporine and methotrexate, while at the same time be treated through the administration of a cell delivery composition.

In one embodiment, the cell delivery composition is administered to a patient to prevent or treat GVHD is administered in a dosage where the GVHD is reduced but where it is not completely eliminated. A low level of GVHD is in some cases beneficial for the stem cell graft to colonize the patient bone marrow. Additional, the presence of active T cells from a donor may help eliminate tumorigenic cells in a subject, such as a subject afflicted with leukemia. The application also provides a method of preventing graft versus host disease in a subject in need of such treatment, the method comprising contacting a transplant, prior to transplantation into the subject, with the cell delivery composition, thereby preventing graft versus host disease in the subject. In one embodiment, a therapeutically effective amount of cell delivery composition is administered to the transplant inoculum prior to transplantation into the subject. In another embodiment, the transplant inoculum is depleted of T cells, such as by centrifugation, and the graft is then treated with IFN-y antagonists prior to implantation into the patient or host.

The application also provides methods of preventing or reducing immune incompatibility in a subject in need thereof, the method including administering to the subject a therapeutically effective amount of a cell delivery composition, wherein the subject is a recipient of a solid organ transplant. In one embodiment, the organ transplant comprises a lung, heart, kidney, liver, or skin. The transplant may be HLA matched or it may be unmatched.

In one embodiment, the solid organ is treated with a cell delivery composition concurrently to organ transplantation or shortly before or after. In another embodiment, the cell delivery composition is administered to the subject as described for treating or preventing GVHD, but wherein a therapeutically effective amount used refers to the amount of cell delivery composition sufficient to show a meaningful subject benefit, i.e., a reduction in the incidence or severity of organ rejection compared to that expected for a comparable group of patients not receiving the cell delivery composition, as determined by the attending physician.

The following examples are for the purpose of illustration only and are not intended to limit the scope of the claims, which are appended hereto.

EXAMPLES

The results herein first validated the immune-modulatory capability of mouse MSCs, then demonstrated increased delivery of targeted firefly luciferase-expressing MSCs to colon, clinical efficacy based on survival, body weight, and histologic scoring and, finally, an increase in the proportion of Treg cells in the colon of targeted mice, indicating a possible mechanism of action of the delivered MSCs.

Results

Ab-Coated MSCs Suppress Splenocyte Proliferation

To examine the potential immunosuppressive capability by MSCs, MSCs were cocultured with freshly isolated splenocytes stimulated by CD3 Ab. In phase contrast microscopic images of 2-day cocultures (FIG. 1a), the splenocytes-only group showed many colonies as indicated arrows, which is indicative of high-proliferative T-cell activity. A decrease in colonies correlated with the increase of MSC number, strongly indicating the inhibition of proliferation in the presence of MSCs.

To quantify the splenocyte proliferation in cocultures with MSCs, 3H-thymidine was added to cocultures and incorporation of $^3$H-thymidine was measured (FIG. 1b). Relative cell proliferation is represented compared to that of the splenocytes-only group. The results demonstrate that MSCs inhibit splenocyte expansion in a dose-dependent fashion. Significant inhibition of splenocyte expansion was observed even at the ratio 1:100 of MSC to splenocytes. Interestingly, vascular cell adhesion molecule Ab-coated MSCs (Ab$_{VCAM-1}$-MSCs) showed statistically enhanced suppressive capability compared to MSC only at dilutions of 1:60 (*P<0.01) and 1:100 (**P<0.05; Student's t-test), possibly representing synergistic effects by anti-VCAM-1 antibodies released from MSCs. The same was not true for Ab$_{MAdCAM}$-MSCs, where the results were statistically indistinguishable from the MSCs only group.

More IV-Delivered Ab$_{VCAM-1}$-MSCs are Found in MLN and Colon Than Uncoated MSC To assess the biodistribution of intravenously injected MSCs, mice were imaged for bioluminescence [see FIG. 2a for the overall bioluminescence imaging (BLI) study design]. C57BL6 mice treated with dextran sulfate sodium (DSS) for 5 days received luciferase-expressing (fluc)-MSCs duallabeled with far-red dye, and were imaged at 2 hours after cell injection. After sacrifice, organs were collected, imaged, and quantified. In BLI of individual organs (FIG. 2b), mice without MSC injection showed no BLI signal. Among MSC injected mice, AbVCAM-1-MSCs showed the strongest signal in mesenteric lymph node (MLN) and colon. The relative BLI difference of Ab$_{VCAM-1}$-MSCs compared to MSCs only is shown in FIG. 2c; data from four independent experiments (N=3-4 mice in each experiment). The results showed a 1.3- and 1.8-fold (*P<0.02, Student's t-test) increase in BLI signal of Ab$_{VCAM-1}$-MSCs mice compared to MSC only in MLN and colon, respectively (FIG. 2c). To test the specificity of binding, AbVCAM-1-MSCs BLI signal was compared to that of isotype Ab control (Abisotype-MSCs) where AbVCAM-1-MSCs showed statistically significant three- to fourfold greater signal (*P<0.05, Student's t-test) in spleen and MLN than Ab$_{isotype}$-MSCs (FIG. 2d). However, although there was a twofold signal difference in colon, this was not statistically significant. The order of decreasing organ BLI signal intensity is: lung, spleen, MLN, and colon. Lung showed a similar signal between AbVCAM-1-MSCs and Ab$_{isotype}$-MSCs, indicating passive entrapment due to MSC size, which has been noted previously.

To confirm the luminescent localization of MSCs in each organ, far-red dye labeled MSCs were imaged using near infrared light, which shows reduced background autofluorescence.28 Representative fluorescent microscopic images are shown in FIG. 2e. Lung tissue was examined as a positive control and was shown to contain many MSCs (purple) in Ab$_{VCAM-1}$-MSCs injected mice whereas the no MSCs injected mice were negative. Several far-red positive MSCs were detected in spleen, MLN, and colon, whereas no signal was detected in noninjected mice, confirming MSCs localization in those organs.

Addressin-MSCs Show Improved Survival Rates in IBD

Figure 3A:
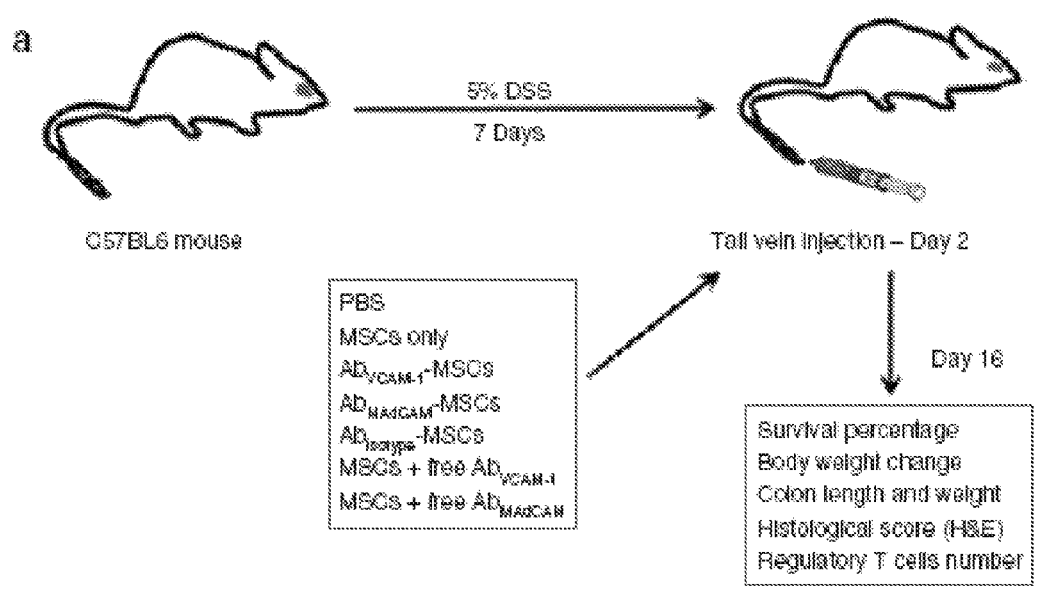
FIG. 3 illustrates survival rate and body weight change in untreated controls, and 5% DS-treated mice injected with vehicle only, MSCs only, or Ab-coated MSCs. (a) Experimental outline and groups. (b) Survival data showing statistically significant survival of $Ab_{MAdCAM}$-MSC compared to PBS (P<0.01), MSC only (P<0.01), $Ab_{isotype}$-MSC (P<0.01), and a strong trend toward significance of $Ab_{VCAM-1}$-MSC compared to PBS (P=0.063), MSC only (P=0.078), Abisotype-MSC (P=0.052). Survival percentage showed statistical significance in overall groups (P=0.04) by Kaplan-Meier log-rank test. (c) Survival rate on MSCs coated with antibodies. Notably, surprising observation was made when Abs-coated MSCs injection was compared with the mixture of MSCs and free antibody. *indicates statistically significant difference between $Ab_{MAdCAM}$-MSC and the mixture of MSC and free MAdCAM antibody (P<0.01). Similar results in body weight change (%) were obtained with survival rate, showing (d) antibody specific therapeutic effects and (e) importance of antibody incorporation on MSCs. Ab, antibody; $Ab_{VCAM-1}$-MSCs, vascular cell adhesion molecule antibody-coated MSCs; DSS, dextran sulfate sodium; MSC, mesenchymal stem cell; PBS, phosphate-buffered saline.

The potential therapeutic effect of MSCs was assessed in an acute experimental colitis model, wherein colitis is induced by 5% DSS in the drinking water over 7 days. At day 2 of oral administration of 5% DSS, mice were tail vein-injected with MSCs and survival rate, body weight change, colon length and weight, histological scores, and the number of regulatory T cells (Tregs) were determined (FIG. 3a).

In the experimental set to investigate potential Ab-specific therapeutic effects (FIG. 3b), Ab$_{MAdCAM-1}$-MSCs (91.7%, 11/12 mice) and Ab$_{VCAM-1}$-MSCs (75%, 9/12) injected mice showed a statistically significant increase on survival rate compared to phosphate-buffered saline (PBS) (41.7%, 5/12), MSCs only (41.7%, 5/12), and Ab$_{isotype}$-MSCs (37%, 3/8) injected mice (Kaplan-Meier log-rank, P=0.036), indicating that anti-mucosal addressin cell adhesion molecule-1 (MAdCAM-1) and VCAM-1 Ab coating specifically increased survival rate. To determine whether the increased survival rates were due to MSCs or due to the presence of anti-MAdCAM-1 or anti-VCAM-1 Ab, mixtures of MSCs and free Ab were injected and survival rate was compared with Ab-coated MSCs (FIG. 3c). The Ab dose was calculated from the amount determined to be present in a typical MSC dose, which is 1.1 µg in 106 cells, or 4.4×10$^6$ Ab molecules per cell. This Ab dose was determined using flow cytometry to quantify the amount of fluorescein isothiocyanate-coated human immunoglobulin G that was bound to MSCs under conditions identical to that used for anti-MAdCAM-1 and anti-VCAM-1 Ab coating (Supplementary Figure S3). This high number of Ab molecules is likely due to some cellular internalization of antibodies.6 Interestingly, when free anti-MAdCAM-1 or anti-VCAM-1 Ab was injected along with uncoated MSCs, the survival rate for free anti-MAdCAM-1 plus MSCs was only 25% (2/8) compared to 91.7% for AbMAdCAM-1-MSCs (*P=0.017) and, although not as impressive, for anti-VCAM-1 plus MSCs, only 50% (4/8). These results indicate that free antiaddressin antibodies alone (1.1 µg/mouse), even if MSCs are coinjected, are not able to increase survival rates in DSS-treated mice.

Therapeutic Measures of IBD

As a therapeutic index, body weight change was also determined Similar to the survival rate, AbMAdCAM-1-MSCs and AbVCAM-1-MSCs showed higher body weight than PBS, MSCs only, and Abisotype-MSCs (FIG. 3d). Also, compared with the mixture of MSC and free Ab, Ab-MSCs showed higher body weight recovery, as shown in FIG. 3e. Both data sets in FIG. 3d and e were statistically significant between 7 and 11 days [analysis of variance (ANOVA), P<0.0001], after which nonsurviving mice skewed the data by being dropped from the body weight measurements. Furthermore, a repeated measures mixed model was conducted using SAS Proc mixed for pairwise tests comparing overall profiles of each group from 3 to 11 days. From this pairwise analysis, AbMAdCAM-1-MSCs showed a statistically significant difference compared to PBS (P<0.02), MSC only (P<0.01), Abisotype-MSCs (P<0.05), and free MAdCAM Ab (P<0.02). AbVCAM-1-MSCs showed significant statistical difference compared to PBS (P<0.04), MSC only (P<0.01), free VCAM-1 Ab (P<0.04), and a strong trend toward significance compared to Abisotype-MSCs (P=0.06).

To assess colonic inflammation, colon length was assessed at day 16 in all surviving mice (FIG. 4a). Recovery in colon length (%) was defined as relative difference compared to PBS-mice, where recovery in wild type and PBS shows 100 and 0%, respectively. Treatment DSS-mice with MSCs showed higher recovery than PBS (ANOVA, P=0.001), indicating that MSCs alone are having at least some therapeutic effect. Notably, AbVCAM-1-MSCs showed a statistically significant difference compared to PBS and Abisotype-MSCs (ANOVA, *P<0.05, Tukey's post hoc test). However, there are no significant differences between MSC only and Ab-MSCs-mice. It should be noted that although there was no significant difference here between MSCs only and addressin-MSCs, most of mice that were likely to show the lowest scores in the MSC-only group had not survived to day 16—only 4/12 MSCs only injected mice survived to day 16, whereas 11/12 AbMAdCAM-1-MSCs and 9/12 AbVCAM-1-MSCs survived.

Examination of the colon from DSS-untreated mice showed a histologically normal structure. However, PBS-injected DSSmice showed transmural necrosis, diffuse loss of crypts, extensive fibrosis, and immune cell infiltration indicated as an arrow (FIG. 4b). Injection of MSCs into DSS-mice significantly decreased the extent and severity of damage in colon although some mild immune cells infiltration is observed in MSC-treated mice. However, AbVCAM-1-MSCs, AbMAdCAM-MSCs injected mice retained normal colon morphology. In blinded histological scores (FIG. 4c), AbVCAM-1-MSCs showed statistical significance with *P<0.01 versus PBS and P<0.05 versus Abisotype-MSCs. MSC only and AbMAdCAM-1-MSCs also significantly presented lower histological scores than PBS, P<0.05 and P<0.01 versus PBS, respectively. However, there was no difference between PBS and Abisotype-MSCs.

Percentage of $T_{reg}$ Cells is Increased in Mice Targeted with MSCs

To examine the number of Treg in treated mice, paraffin-sectioned colons were double-immunostained with CD3 Ab (T-cell marker), Foxp3 (Treg, intracellular marker) and 4'-6-diamidino-2-phenylindole, and fluorescent microscopic images were captured, and the differently stained cells quantified. A representative $CD3^+Foxp3^+$ cell image is shown in FIG. 5a, where Tregs are colocalized with Foxp3 Ab staining, 4'-6-diamidino-2-phenylindole nuclear staining, and surface expression of CD3. PBS-injected mice showed a high number of $CD3^+T$ cell in the colon whereas MSC-mice showed a low number as shown in FIG. 5a. Total percentage of Treg is shown in FIG. 5b, demonstrating that treatment of DSS-mice with MSCs increased the percentage of Tregs with statistical significance (ANOVA, P<0.0001). Interestingly, AbVCAM-1-MSCs showed statistical difference compared to PBS and MSC only (ANOVA, *P<0.05, Tukey's post hoc test).

Having described the invention, the following is claimed:

1. A method of treating inflammatory bowel disease in a subject, the method comprising:
administering a therapeutically effective amount of a cell delivery composition to the subject, the cell delivery composition comprising an mesenchymal stem cell and a plurality of targeting moieties that bind to endothelial cell adhesion molecules expressed by endothelial cells in the colon and small intestine of the subject, the targeting moieties being coated on and linked to the mesenchymal stem cell and enhancing adherence of the mesenchymal stem cell to an endothelial colon and small intestine cell of the subject when administered to the subject systemically, wherein the cell delivery composition suppresses inflammation in the colon and small intestine of the subject.

2. The method of claim 1, the endothelial cell adhesion molecule comprising an immunoglobulin superfamily cell adhesion molecule selected from the group consisting of ICAM1, ICAM2, ICAM3, VCAM1, and MAdCAM.

3. The method of 1, wherein the plurality of targeting moieties comprises an antibody or fragment thereof that binds to an endothelial cell adhesion molecule.

4. The method of claim 1, wherein the cell delivery composition is administered to the subject by intravenous injection.

5. The method of claim 1, wherein the endothelial cell is an activated endothelial cell.

6. The method of claim 1, wherein the mesenchymal stem cell is pre-coated with a linker.

7. The method of claim 6, wherein the linker is selected from protein G and protein A.

8. The method of claim 1, wherein the mesenchymal stem cell is directly linked to the plurality of targeting moieties.

9. The method of claim 8, wherein the plurality of targeting moieties are modified with a lipophilic moiety.

10. The method of claim 1, wherein the mesenchymal stem cell is an allogeneic mesenchymal stem cell.

11. The method of claim 1, wherein the mesenchymal stem cell is an autologous mesenchymal stem cell.

12. The method of claim 1, the endothelial cell adhesion molecule comprising MAdCAM.

* * * * *